(12) United States Patent
McClintock

(10) Patent No.: US 11,771,474 B2
(45) Date of Patent: Oct. 3, 2023

(54) BAND TENSIONING SYSTEM

(71) Applicant: K2M, Inc., Leesburg, VA (US)

(72) Inventor: Larry McClintock, Gore, VA (US)

(73) Assignee: K2M, Inc., Leesburg, VA (US)

( * ) Notice: Subject to any disclaimer, the term of this patent is extended or adjusted under 35 U.S.C. 154(b) by 324 days.

(21) Appl. No.: 16/765,019

(22) PCT Filed: Dec. 14, 2018

(86) PCT No.: PCT/US2018/065684
§ 371 (c)(1),
(2) Date: May 18, 2020

(87) PCT Pub. No.: WO2019/118844
PCT Pub. Date: Jun. 20, 2019

(65) Prior Publication Data
US 2020/0352610 A1    Nov. 12, 2020

Related U.S. Application Data

(60) Provisional application No. 62/598,736, filed on Dec. 14, 2017.

(51) Int. Cl.
| A61B 17/70 | (2006.01) |
| A61B 17/84 | (2006.01) |
| A61B 17/88 | (2006.01) |

(52) U.S. Cl.
CPC ...... *A61B 17/7053* (2013.01); *A61B 17/7032* (2013.01); *A61B 17/842* (2013.01); *A61B 17/8869* (2013.01)

(58) Field of Classification Search
CPC ............ A61B 17/7053; A61B 17/7022; A61B 17/7029; A61B 17/7031; A61B 17/7005; A61B 17/7014
See application file for complete search history.

(56) References Cited

U.S. PATENT DOCUMENTS

| 5,782,831 A * | 7/1998 | Sherman ............ A61B 17/7079 606/279 |
| 6,248,106 B1 * | 6/2001 | Ferree ................ A61B 17/7022 606/328 |
| 7,473,267 B2 | 1/2009 | Nguyen et al. |
| 9,433,441 B2 | 9/2016 | George et al. |
| 10,034,692 B2 | 7/2018 | Palmer et al. |
| 10,548,644 B2 | 2/2020 | George et al. |

(Continued)

FOREIGN PATENT DOCUMENTS

| WO | 2012023909 A1 | 2/2012 |
| WO | 2020033870 A1 | 2/2020 |

OTHER PUBLICATIONS

International Search Report for PCT/US2018/065684 dated Mar. 5, 2019; 2 pages.

(Continued)

*Primary Examiner* — Julianna N Harvey
(74) *Attorney, Agent, or Firm* — Lerner David LLP

(57) ABSTRACT

A band tensioner includes a shank, a head, and a tensioning mechanism disposed within the head. The shank is configured to secure the band tensioner to a first bony element and the head is secured to an end of the shank. The tensioning mechanism is configured to lengthen and shorten a flexible implant relative to the head of the band tensioner.

19 Claims, 11 Drawing Sheets

(56) References Cited

U.S. PATENT DOCUMENTS

| | | | |
|---|---|---|---|
| 10,575,879 B2 | 3/2020 | Palmer et al. | |
| 2006/0235416 A1 | 10/2006 | Revis | |
| 2010/0004692 A1* | 1/2010 | Biedermann | A61B 17/8685 |
| | | | 606/301 |
| 2010/0318129 A1* | 12/2010 | Seme | A61B 17/7001 |
| | | | 606/279 |
| 2012/0165866 A1 | 6/2012 | Kaiser et al. | |
| 2015/0201973 A1* | 7/2015 | Lindemann | A61B 17/7053 |
| | | | 606/279 |
| 2016/0324546 A1 | 11/2016 | Simpson et al. | |
| 2016/0324547 A1* | 11/2016 | Miller | A61B 17/7032 |
| 2020/0000505 A1* | 1/2020 | Vitale | A61B 17/7031 |
| 2020/0085471 A1* | 3/2020 | McClintock | A61B 17/8625 |
| 2020/0170696 A1* | 6/2020 | Haber | A61B 17/809 |
| 2021/0290271 A1* | 9/2021 | Daniels | A61B 17/7008 |

OTHER PUBLICATIONS

International Search Report including Written Opinion for PCT/US2018/065684 dated Mar. 5, 2019; 9 pages.

Extended European Search Report including Written Opinion for EP18888971.1 dated Jun. 8, 2021; 9 pages.

* cited by examiner

BAND TENSIONING SYSTEM

CROSS-REFERENCE TO RELATED APPLICATION

This application is a national stage phase entry under 35 U.S.C. § 371 of International Application No. PCT/US2018/065684, filed Dec. 14, 2018, which claims priority to, and the benefit of, U.S. Provisional Patent Application Ser. No. 62/598,736, filed Dec. 14, 2017, the entire contents of which are hereby incorporated by reference.

BACKGROUND

1. Technical Field

The present disclosure relates to implants and, more specifically, to a tensioning system for tensioning a band secured to an implant.

2. Discussion of Related Art

The spine is made up of a superposition of vertebrae, that are normally aligned along a vertebral axis, extending from the lumbar vertebrae to the cervical vertebrae, with each vertebra presenting a posterior wall from which a spinous process projects and two side edges having walls from which the ribs and/or transverse processes project. When an individual's spine presents abnormal curvature, the vertebrae are inclined relative to one another and relative to said vertebral axis. The lateral edges of the vertebrae situated on one side are thus closer to one another and form a concave curve, while the lateral edges on the other side appear spaced apart from one another and form a convex curve. In order to straighten the spinal column, the lateral edges of the vertebrae on the concave side are spaced apart from one another and are taken relative to one another to a distance that is substantially equivalent to the distance between the lateral edges on the other side. Thereafter, in order to keep the vertebrae in that position relative to one another, known devices are used that have screws for insertion into the vertebrae or hooks for inserting along the inside wall of the spinal canal, associated with rods for interconnecting the screws or the hooks.

The hooks are generally inserted in pairs in each vertebra and on either side close to the pedicles, the heads of the hooks projecting from the posterior wall of a vertebra, one on either side of the spinous process. The heads may be tulip-shaped to receive a rod that is secured by means of a set screw inserted in the head and bearing against the rod. Rows constituted by the heads of the hooks situated on either side of the spinous processes are interconnected and held in fixed position by two rods that are parallel to each other and to the axis of the spine.

The screws have tulip-shaped heads and are inserted in pairs in the posterior walls of vertebrae in the pedicles on either side of the spinous processes. The screws constitute fastening points in the vertebrae for holding them relative to one another. The screws are inserted into the pedicles of the vertebrae, and under certain circumstances, the pedicles may be damaged.

Some spinal constructs include flexible bands that secure portions of a spinal construct to one another and/or to a bony element of a patient.

There is a continuing need for an implant that tensions and locks flexible bands about portions of a spinal construct and/or bony elements.

SUMMARY

In an aspect of the present disclosure, a band tensioner includes a shank, a head, and a tensioning mechanism disposed within the head. The shank is configured to secure the band tensioner to a first bony element and the head is secured to an end of the shank. The tensioning mechanism is configured to lengthen and shorten a flexible implant relative to the head of the band tensioner.

In aspects, the tensioning mechanism may include a band shaft that defines a shaft axis and a slot therethrough. The slot may be configured to receive a portion of the flexible implant such that the flexible implant is wound around the band shaft in response to rotation of the band shaft about the shaft axis in a first direction and is unwound from about the shaft in response to rotation of the band shaft about the shaft axis in a second direction opposite the first direction. The tensioning mechanism may include a tensioning gear that defines a drive axis. The tensioning gear is operably associated with the band shaft such that rotation of the tensioning gear in a first drive direction about the drive shaft rotates the band shaft in the first direction and rotation of the tensioning gear in the second drive direction opposite the first drive direction rotates the band shaft in the second direction. The drive axis may be perpendicular to the shaft axis. The tensioning mechanism may include a retainer that is received within the head and is engaged with the band shaft and the tensioning gear to secure the band shaft and the tensioning gear within the head. The retainer may be removable from the head.

In some aspects, the shank may define a longitudinal axis of the band tensioner and the shaft axis may be perpendicular to the longitudinal axis. The shank may define a channel. The shank may be configured to pass entirely through a bony element such that the channel is defined entirely through the bony element.

In another aspect of the present disclosure, a spinal construct includes a flexible implant and a band tensioner. The band tensioner includes a shank, a head, and a tensioning mechanism. The bony element is configured to secure the band tensioner to a bony element. The head is secured to an end of the shank. The tensioning mechanism is disposed within the head and is configured to lengthen and shorten the flexible implant relative to the head of the band tensioner.

In aspects, the tensioning mechanism may include a band shaft that defines a shaft axis and defines a slot. The slot may receive a portion of the flexible implant such that the flexible implant is wound around the band shaft in response to rotation of the band shaft about the shaft axis in a first direction and is unwound from about the shaft in response to rotation of the band shaft about the shaft axis in a second direction opposite the first direction. The tensioning mechanism may include a tensioning gear that defines a drive axis. The tensioning gear is operably associated with the band shaft such that rotation of the tensioning gear in a first drive direction about the drive axis rotates the band shaft in the first direction and rotation of the tensioning gear in a second drive direction opposite the first drive direction rotates the band shaft in the second direction. The drive axis may be perpendicular to the shaft axis.

In some aspects, the shank may define a channel that passes therethrough. The shank may be configured to pass entirely through a bony element such that the channel is defined entirely through the bony element.

In another aspect of the present disclosure, a method of correcting a defect of a spine includes securing a band tensioner to a vertebra of the spine, securing a flexible implant within a tensioning mechanism of the band tensioner, and tensioning the flexible implant with the tensioning mechanism.

In aspects, securing the band tensioner to the vertebra may include passing a shank of the band tensioner through the vertebra. Securing the flexible implant within the tensioning mechanism may include passing the flexible implant through a channel defined by the shank such that the flexible implant passes entirely through the vertebra.

In aspects, securing the flexible implant within the tensioning mechanism may include passing the flexible implant through a slot defined in a band shaft of the tensioning mechanism. Tensioning the flexible implant may include rotating the band shaft about a shaft axis such that the flexible implant is wound around the band shaft.

In some aspects, securing the band tensioner to the vertebra may include passing a tip of a driver through a first opening in a head of the band tensioner to rotate the band tensioner about a longitudinal axis thereof to thread a shaft of the band tensioner into the vertebra. Tensioning the flexible implant may include passing the tip of the driver through a second opening in the head of the band tensioner which is offset form the first opening to rotate a tensioning gear of the tensioning mechanism.

In certain aspects, the tensioning the flexible implant may include engaging an opening the head with a tip of an alignment tool to rotatably fix the tensioner about a longitudinal axis thereof and passing a driver through a driver channel of the alignment tool such that a tip of the driver passes through the tip of the alignment tool to engage a tensioning gear of the tensioning mechanism.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Figure 1:
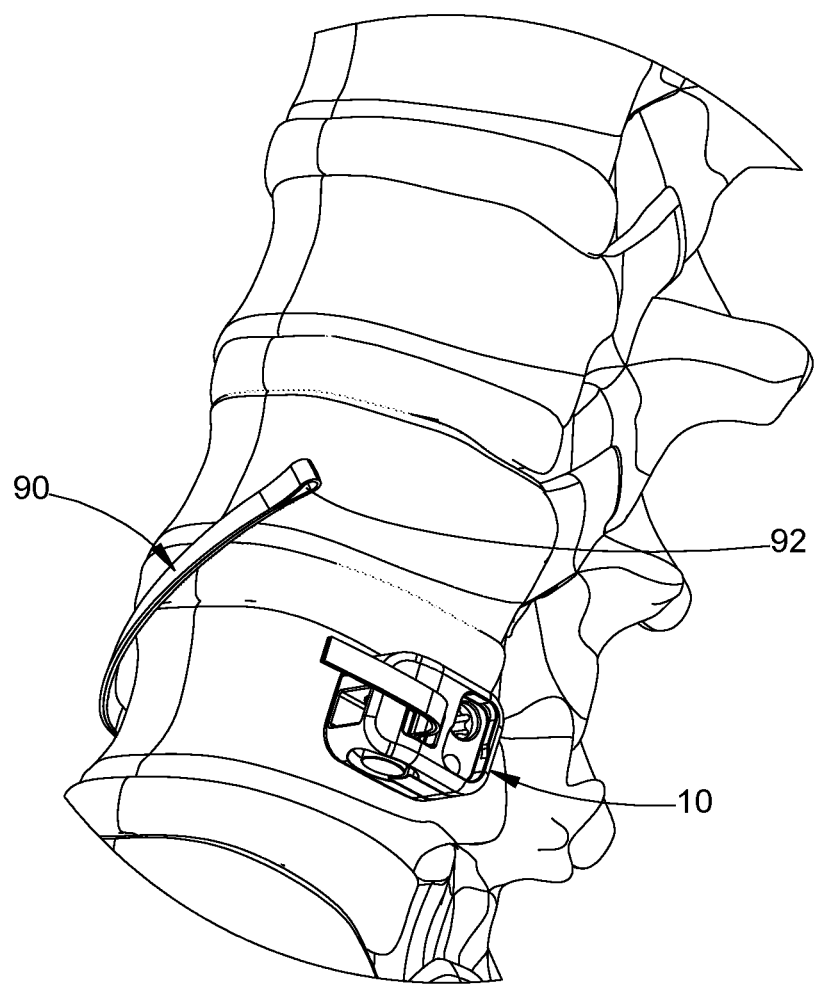
FIG. 1 is a perspective view of a portion of a spine with a band tensioner provided in accordance with the present disclosure secured to a vertebra of the spine.

Embodiments of the present disclosure are now described in detail with reference to the drawings in which like reference numerals designate identical or corresponding elements in each of the several views. As commonly known, the term "clinician" refers to a doctor, a nurse or any other care provider and may include support personnel. Additionally, the term "proximal" refers to the portion of the device or component thereof that is closer to the clinician and the term "distal" refers to the portion of the device or component thereof that is farther from the clinician. In addition, the term "cephalad" is known to indicate a direction toward a patient's head, whereas the term "caudal" indicates a direction toward the patient's feet. Further still, the term "lateral" is understood to indicate a direction toward a side of an instrument or body of the patient, i.e., away from the middle of the body of the patient when relative to the body. The term "posterior" indicates a direction toward the patient's back, and the term "anterior" indicates a direction toward the patient's front. Additionally, terms such as front, rear, upper, lower, top, bottom, and similar directional terms are used simply for convenience of description and are not intended to limit the disclosure. In the following description, well-known functions or constructions are not described in detail to avoid obscuring the present disclosure in unnecessary detail.

This disclosure relates generally to spinal constructs including band tensioners. The band tensioners are configured to tension flexible implants or bands of the spinal constructs. The band tensioners include a head, a shank, and a tensioning mechanism disposed within the head. The tensioning mechanism includes a band shaft and a tensioning gear. The flexible implant passes through a slot in the band shaft and the tensioning gear is coupled with the band shaft such that rotation of the tensioning gear rotates the band shaft such that the flexible implant is tensioned or relaxed depending on the direction of the rotation of the tensioning gear.

Referring to FIG. 1, a spinal construct is provided in accordance with the present disclosure and includes a band tensioner 10 and a flexible implant 90. The spinal construct 1 detailed herein may be used to secure elements to the spine of a patient to correct a curvature of the spine.

Figure 3:
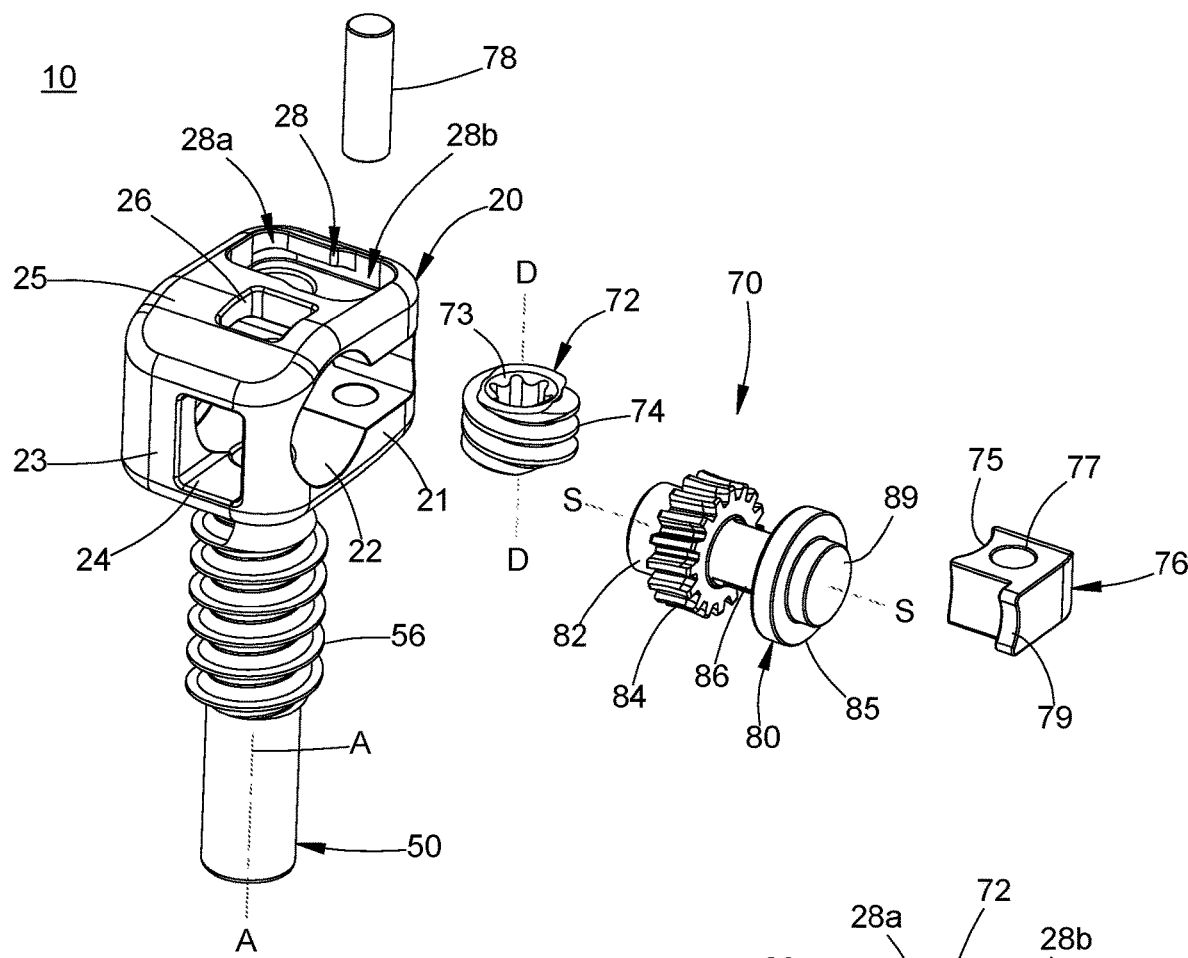
FIG. 3 is an exploded view, with parts separated, of the band tensioner of FIG. 2.
Figure 2:
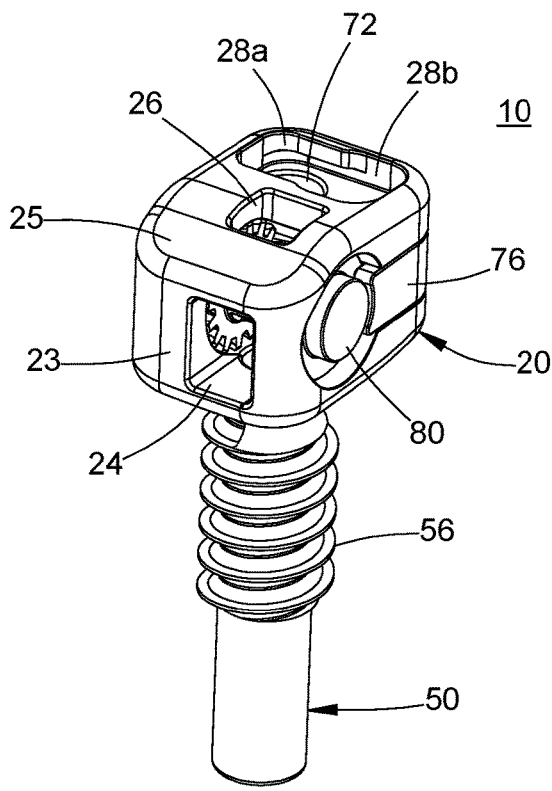
FIG. 2 is a perspective view of the band tensioner of FIG. 1.
Figure 4:
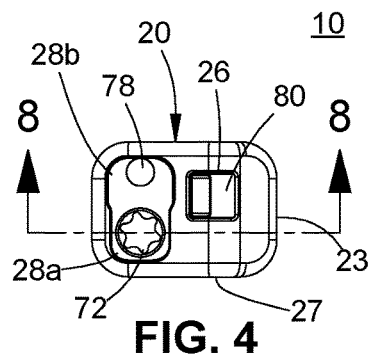
FIG. 4 is a top view of the band tensioner of FIG. 2.

With reference to FIGS. 2 and 3, the band tensioner 10 includes a head 20, a shank 50, and a tensioning mechanism 70. The shank 50 extends from the head 20 and is configured to secure the band tensioner 10 to a bony element of a patient, e.g., a vertebra. The outer surface of the shank 50 may include a threaded portion 56 configured to secure the shank 50 within the bony element. The threaded portion 56 may extend the entire length of the shank 50 or may only be disposed along a portion of the shank 50. The shank 50 defines a band channel 54 (FIG. 9) that allows a flexible implant, e.g., flexible implant 90, to enter the band tensioner 10 by passing through the bony element of the patient and into the tensioning mechanism 70 as detailed below.

The head 20 of the band tensioner 10 includes the tensioning mechanism 70 that is configured to receive, tension, and lock the flexible implant 90 relative to the band tensioner 10. The head 20 includes a back surface 21 and a side surface 23 adjacent the back surface 21. The back surface 21 defines a drive opening 22 that passes through the back surface 21 of the head 20 and the side surface 23 defines a side opening 24. The head 20 also includes a top surface 25 that is opposite the shank 50 and adjacent both the back surface 21 and the side surface 23. The top surface 25 defines a band opening 26 and a tensioning opening 28a that is laterally offset from the band opening 26. The tensioning opening 28a is defined in a side of the top surface 25 opposite the side surface 23.

The tensioning mechanism 70 is passed through the drive opening 22 to position the tensioning mechanism 70 within the head 20. The tensioning mechanism 70 includes a drive gear 72 and a band shaft 80 that are each passed through the drive opening 22. The drive gear 72 is aligned with the tensioning opening 28a such that the drive gear 72 is rotatable about a drive axis D-D that passes through the tensioning opening 28. The drive gear 72 includes a helical thread 74 on an outer surface of the drive gear 72 that wraps around a drive axis D-D. The helical thread 74 is configured to engage a portion of the band shaft 80 as detailed below. The drive gear 72 also defines a drive socket 73 in a top surface of the drive gear 72 that is coaxial with the drive axis D-D. The drive socket 73 can have a plurality of geometries including, but not limited to, square, star, cross, hexagonal, or slot.

Figure 5:
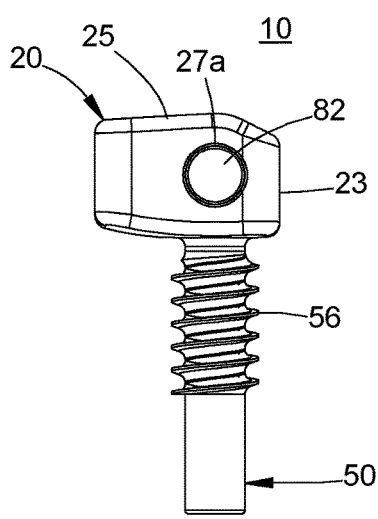
FIG. 5 is a front view of the band tensioner of FIG. 2.
Figure 6:
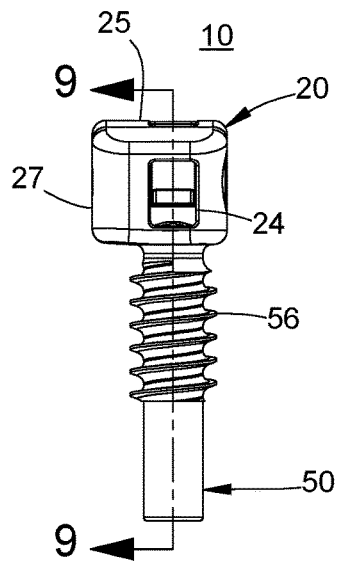
FIG. 6 is a right view of the band tensioner of FIG. 2.
Figure 7:
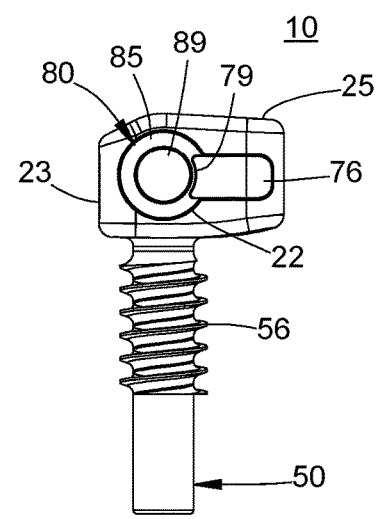
FIG. 7 is a back view of the band tensioner of FIG. 2.
Figure 9:
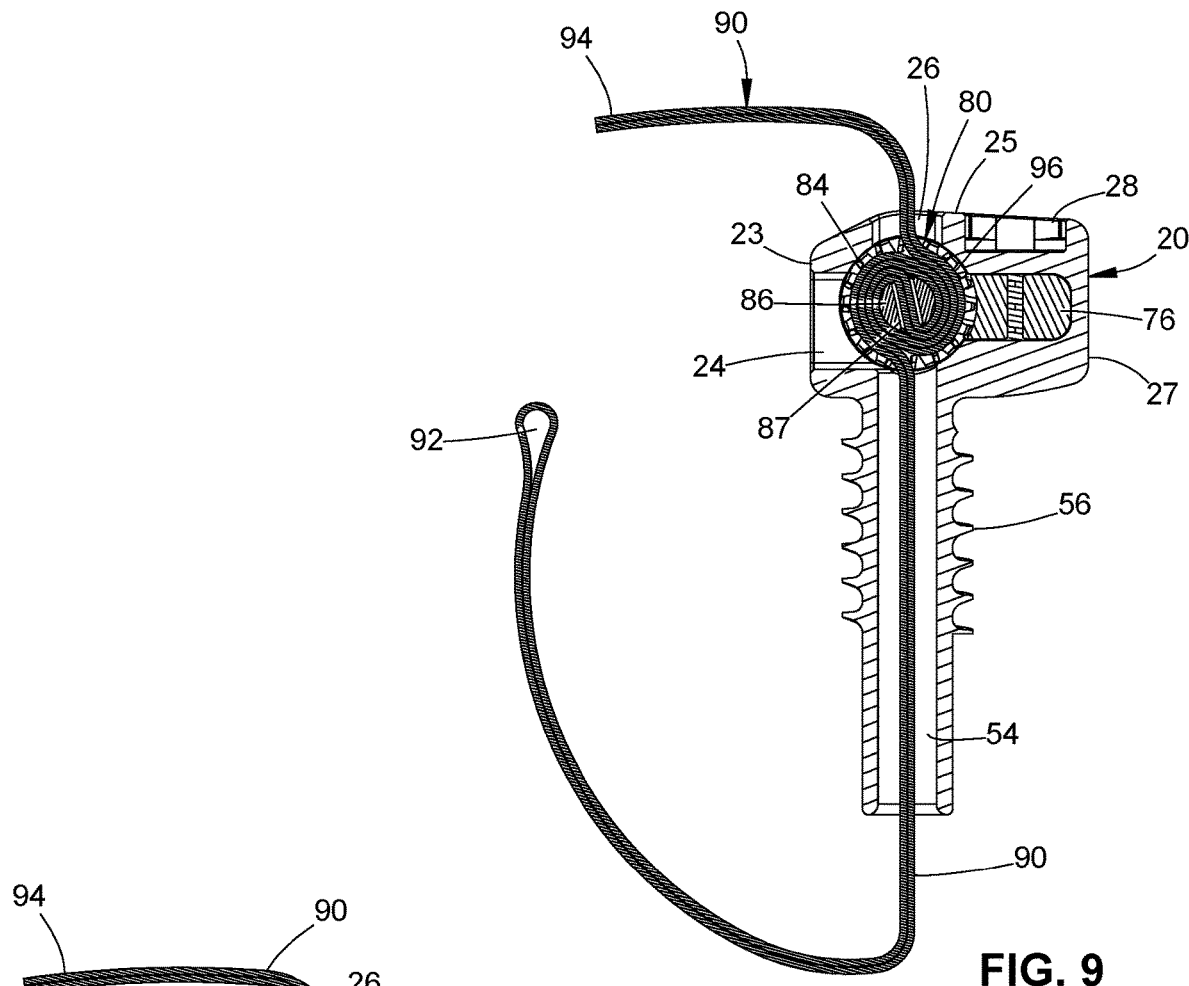
FIG. 9 is a cross-sectional view taken along the section line 9-9 of FIG. 4 with a band entering through a shank of the band tensioner.

The band shaft 80 defines, and is rotatable about, a shaft axis S-S that is transverse to the drive axis D-D. The band shaft 80 is passed through the drive opening 22 and secured within the head 20 adjacent the side surface 23. The band shaft 80 includes, from a front end to a back end, a front portion 82, a tensioning gear 84, a slotted section 86, a retention ring 85, and a back portion 89. The front portion 82 is cylindrical in shape is received within a front opening 27a (FIG. 5) in a front surface 27 of the head 20 when the band shaft 80 is disposed within the drive opening 22. The front portion 82 may be polished or have a low friction coating to allow band shaft 80 to freely rotate within the drive opening 22 about the shaft axis S-S with the front portion 82 received within the front opening 27a. Alternatively, the front portion 82 may have a high friction coating and/or features to engage the front opening 27a of the head 20 such that the band shaft 80 resists rotation about the shaft axis S-S. The front portion 82 may have a length along the shaft axis S-S to position the tensioning gear 84 such that the tensioning gear 84 meshingly engages the helical thread 74 of the drive gear 72. The tensioning gear 84 extends radially beyond the front portion 82 and is rotatably fixed to the band shaft 80. The tensioning gear 84 may be formed separate from the band shaft 80 and fixed to the band shaft 80 by welding. The front portion 82 may also retain the tensioning gear 84 on the band shaft 80. In some embodiments, the tensioning gear 84 is monolithically formed with the band shaft 80. The slotted section 86 is disposed between the tensioning gear 84 and the retention ring 85. The slotted section 86 includes a band slot 87 passing entirely through the band shaft 80 (FIG. 9). The band slot 87 is configured to receive the flexible implant 90 therethrough as detailed below. The retention ring 85 is configured to be engaged by a retainer 76 such that the band shaft 80 is secured within the drive opening 22 of the head 20. The back portion 89 of the band shaft 80 extends from the retention ring 85 and has a diameter smaller than the diameter of the retention ring 85. The back portion 89 may be engaged by the retainer 76 to position the band shaft 80 within the drive opening 22 while allowing the band shaft 80 to rotate about the shaft axis S-S (FIG. 3).

Figure 8:
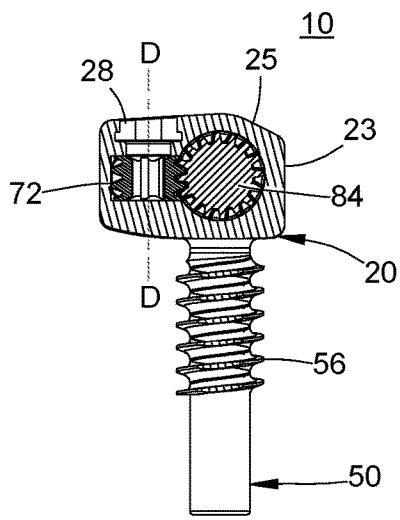
FIG. 8 is a cross-sectional view taken along the section line 8-8 of FIG. 4.

With continued reference to FIGS. 2 and 3, the retainer 76 is positioned within the drive opening 22 to position and retain the drive gear 72 and the band shaft 80 within the drive opening 22. Specifically, the retainer 76 includes a gear recess 75 and a shaft retainer 79. The retainer 76 defines a passage 77 that extends through the retainer 78 parallel to the longitudinal axis A-A. The passage 77 receives a retention pin 78 that passes through a pin opening 28b to secure the retainer 76 within the drive opening 22. When the retention pin 78 is received within the passage 77, the gear recess 75 receives the drive gear 72 to position the drive gear 72 within the drive opening 22. As shown, the gear recess 75 defines an arc about the drive axis D-D. When the retention pin 78 is received within the passage 77, the shaft retainer 79 extends over a portion of the retention ring 85 to secure the band shaft 80 within the drive opening 22 and may engage the back portion 89 to position the band shaft 80 within the drive opening 22 (FIG. 8).

With reference to FIG. 9, the flexible implant 90 passes through the band tensioner 10 which is configured to shorten and lengthen the flexible implant 90 relative to the band tensioner 10. Specifically, the flexible implant 90 forms a loop 92 that is configured to be disposed about a bony element and/or may be coupled other elements of a spinal construct (not shown).

The flexible implant 90 enters the band tensioner 10 through the band opening 26 defined in the top surface 25 of the head 20. A central portion 96 of the flexible implant 90 passes through the band slot 87 of the slotted section 86 of the band shaft 80. The loop 92 of the flexible implant 90 exits the band tensioner 10 through the band channel 54 defined through the shank 50. The shank 50 may be passed through a bony element of such that the head 20 is disposed on a first side of the bony element and the shank 50 exits a second opposite side of the bony element.

The flexible implant 90 wraps around the slotted section 86 of the band shaft 80 such that as the band shaft 80 is rotated in a first shaft direction about the shaft axis S-S (FIG. 3). The loop 92 has a pre-determined size. It is contemplated that the size of the opening of the loop 92 may be variable.

Referring briefly back to FIGS. 3 and 8, the tensioning gear 84 and the drive gear 72 are meshingly engaged with one another such that rotation of the drive gear 72 about the drive axis D-D rotates the band shaft 80 about the shaft axis S-S. Specifically, as the drive gear 72 is rotated in a first drive direction about the drive axis D-D, the band shaft 80 is rotated in the first shaft direction and when the drive gear 72 is rotated in a second, opposite drive direction about the drive axis D-D, the band shaft 80 is rotated in the second, opposite shaft direction.

Figure 10:
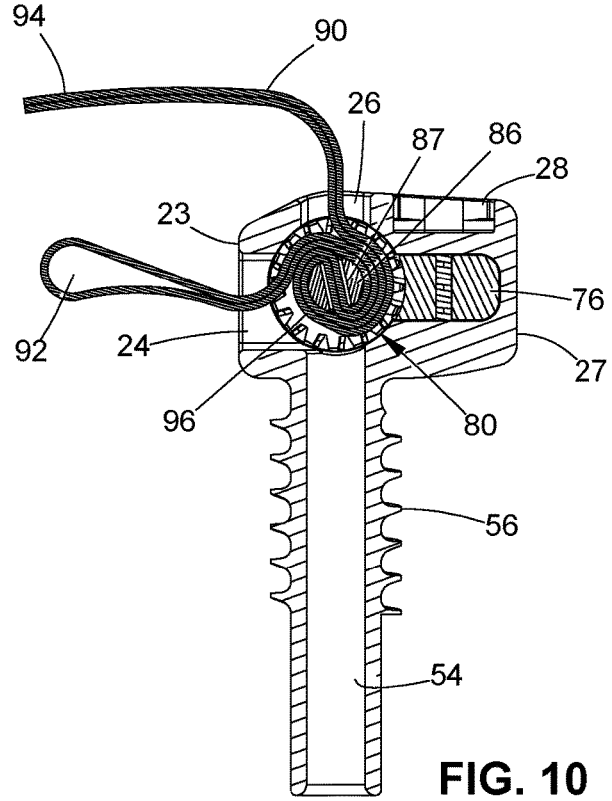
FIG. 10 is a cross-sectional view of the band tensioner of FIG. 9 with the band entering the band tensioner laterally.

With reference to FIG. 10, the loop 92 may exit the band tensioner 10 through the side opening 24 in the side surface 23 of the head 20 such that the loop 92 exits the band tensioner 10 on the same side of a bony element that the flexible implant 90 enters the band opening 26. It is contemplated that a first side of the loop 92 may exit the band tensioner 10 through the side opening 24 and a second side of the loop 92 may exit the band tensioner through the band channel 54 such that the loop 92 wraps around a bony element.

Figure 11:
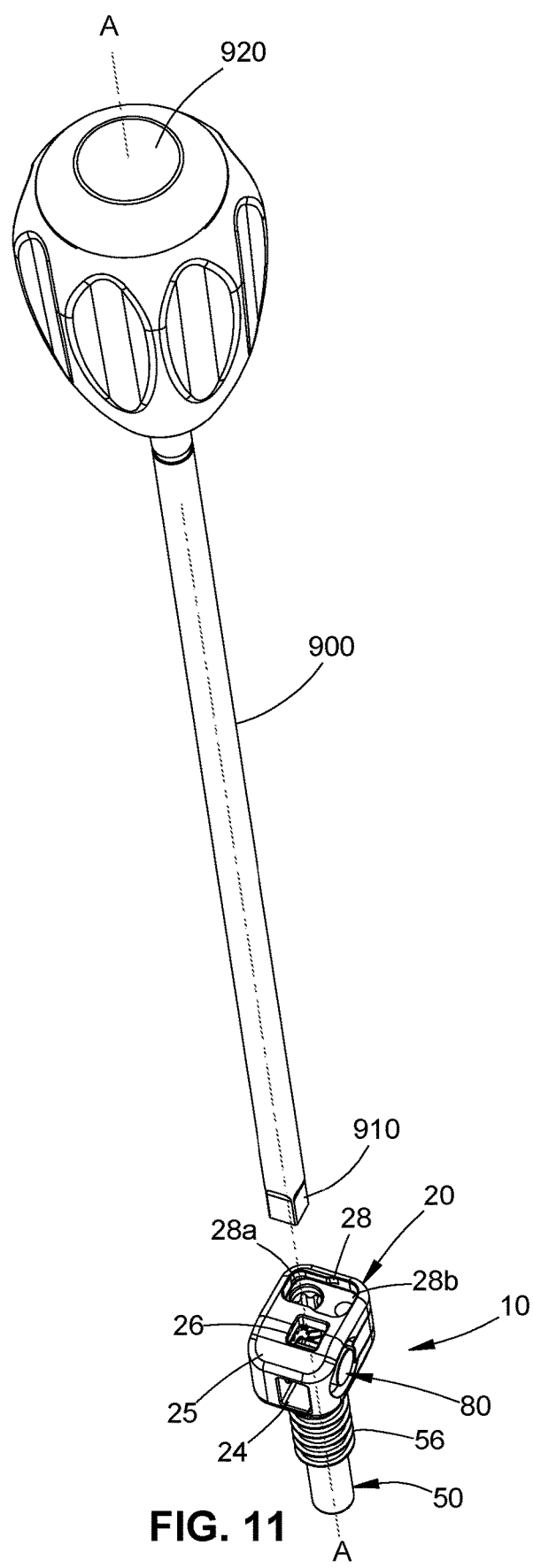
FIG. 11 is perspective view of a driver approaching the band tensioner of FIG. 1.
Figure 12:
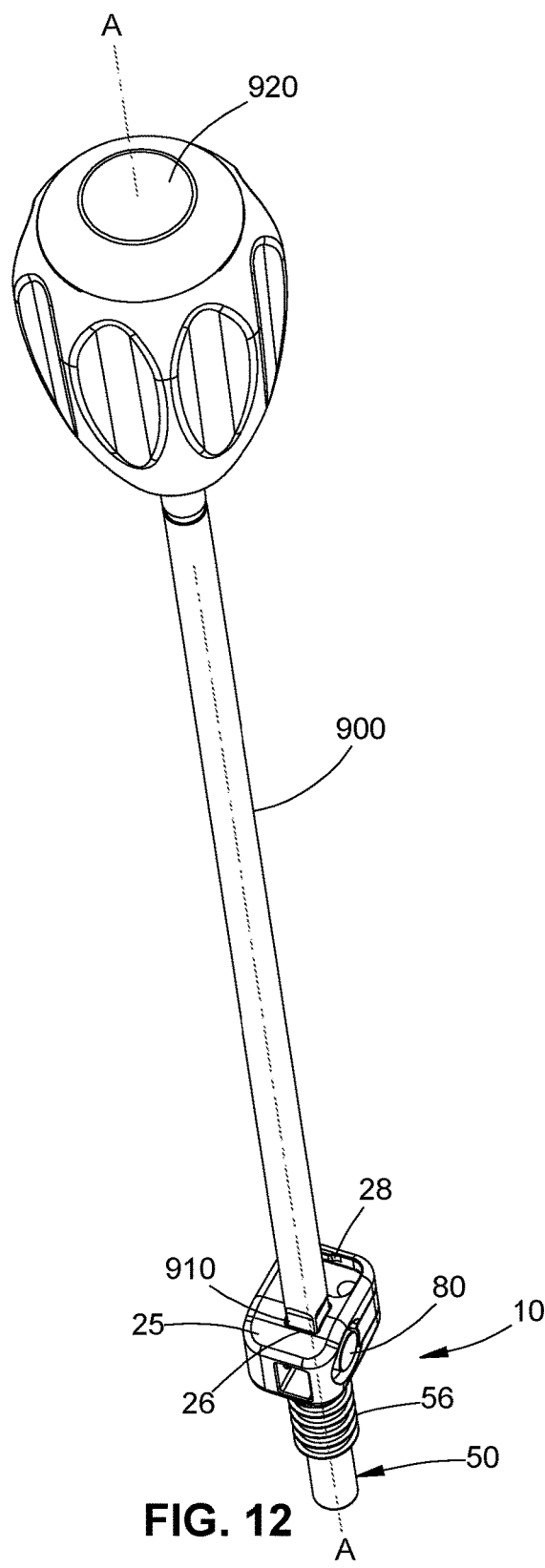
FIG. 12 is a perspective view of the driver engaged with a top band opening of the band tensioner of FIG. 1.

With additional reference to FIGS. 11 and 12, the band tensioner 10 may be used with a driver 900 to secure the band tensioner 10 to a bony element. The driver 900 includes a tip 910 that is sized to be received within the band opening 26 in the top surface 25 of the head 20. When the tip 910 is received within the band opening 26, the driver 900 can be rotated to rotate the band tensioner 10 about the longitudinal axis A-A of the shank 50 such that the band tensioner 10 can be driven into a bony element. Specifically, the shank 50 may be inserted into a hole in the bony element. The hole may be drilled or created by another suitable means. The threaded portion 56 of the shank 50 may engage the bony element to secure the band tensioner 10 to the bony element. The driver 900 may include a band channel 920 that passes entirely through the driver 900 and allows the flexible implant 90 to pass through the driver 900.

Figure 13:
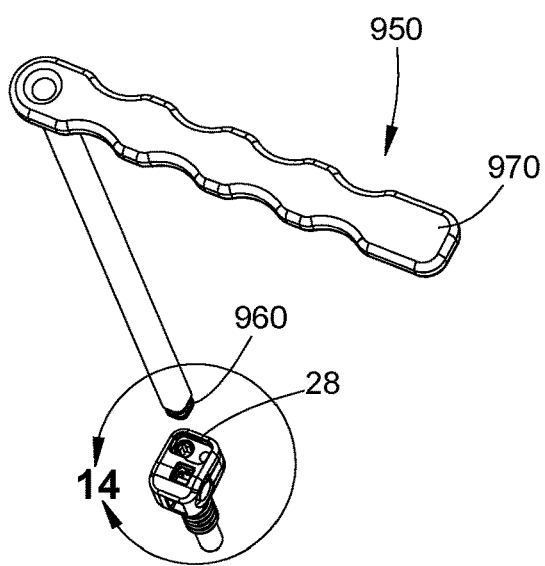
FIG. 13 is a perspective view of an alignment tool approaching the band tensioner of FIG. 1.
Figure 14:
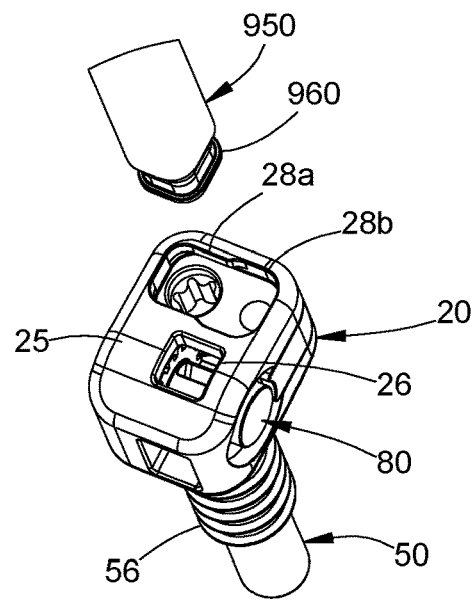
FIG. 14 is an enlarged view of the indicated are of detail of FIG. 13.
Figure 15:
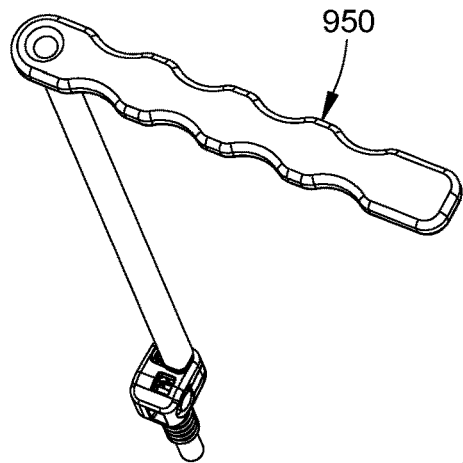
FIG. 15 is a perspective view of an alignment tool engaged with a first portion of a tensioning opening of the band tensioner of FIG. 1.
Figure 16:
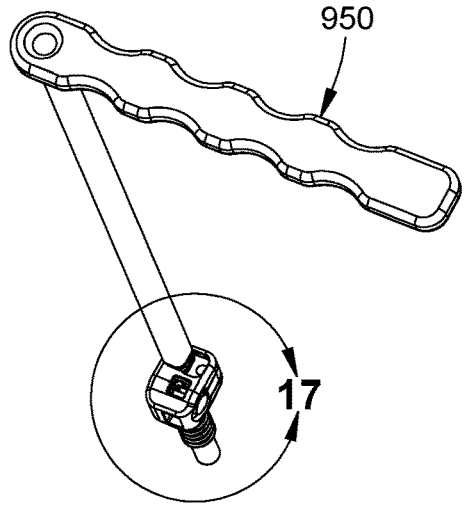
FIG. 16 is a perspective view of the alignment tool engaged with a second portion of the tensioning opening of the band tensioner of FIG. 1.
Figure 17:
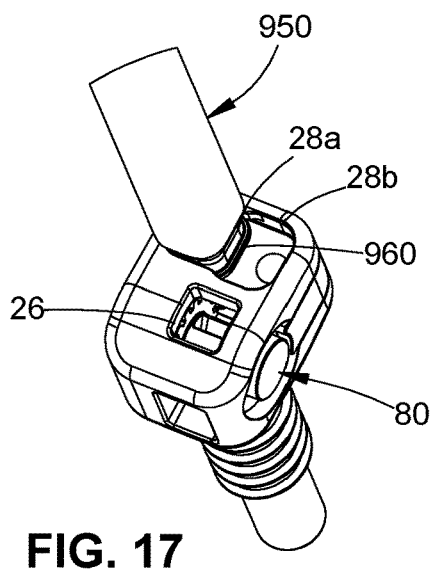
FIG. 17 is an enlarged view of the indicated area of detail of FIG. 16.

Referring now to FIGS. 13-17, the alignment tool 950 includes a tip 960 that engages portions of the tensioning opening 28 of the head 20. As shown in FIGS. 13-15, the tip 960 is engaged with a back portion 28a of the tensioning opening 28 such that the alignment tool 950 can manipulate the band tensioner 10 and/or the flexible band 90 that passes through the head 20 of the band tensioner 10. For example, the flexible band 90 may be drawn through the band tensioner 10 such that the flexible band 90 passes through the band slot 87 in the band shaft 80.

Referring now to FIGS. 16-19, the alignment tool 950 is positioned with the tip 960 received within the front portion 28b of the tensioning opening 28. The alignment tool 950 includes a handle 970 that extends from the alignment tool 950 transverse to a longitudinal axis of the alignment tool 950. The handle 970 may be used to prevent rotation of the alignment tool 950 and/or the band tensioner 10 relative to the bony element.

Figure 18:
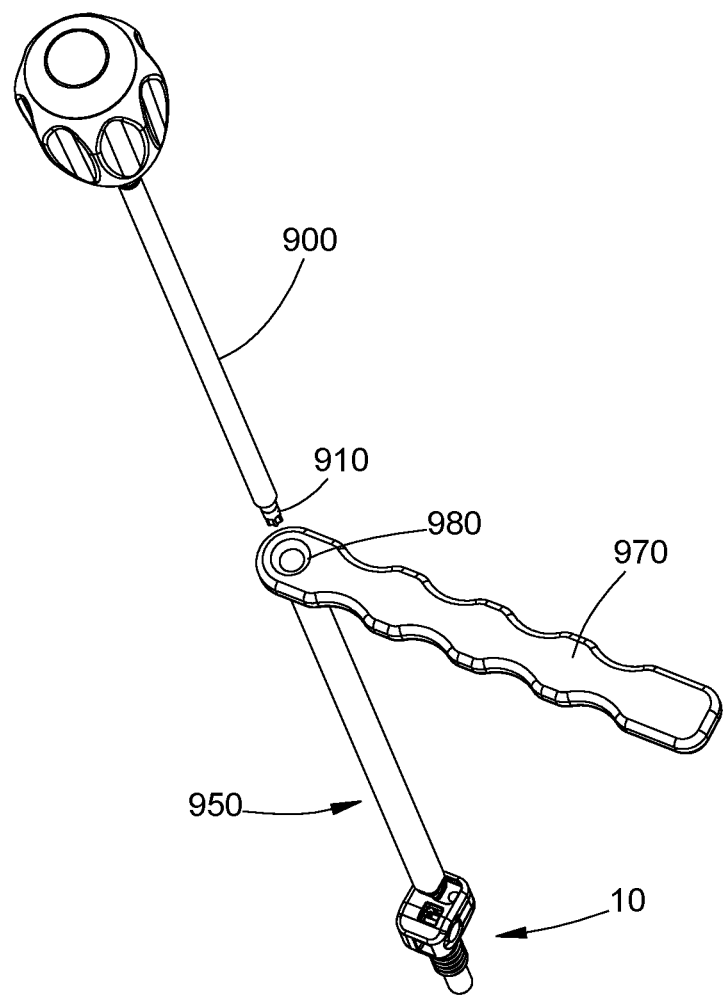
FIG. 18 is a perspective view of the driver approaching a guide channel of the alignment tool with the alignment tool engaged with the second portion of the tensioning opening of the band tensioner as shown in FIG. 16.
Figure 19:
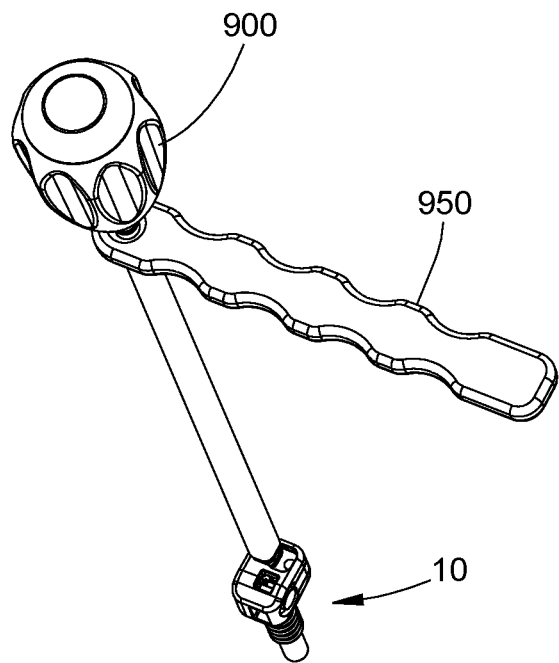
FIG. 19 is a perspective view with the driver passed through the guide channel of the alignment tool to engage a tensioning gear of the band tensioner of FIG. 1.
Figures 20, 21:
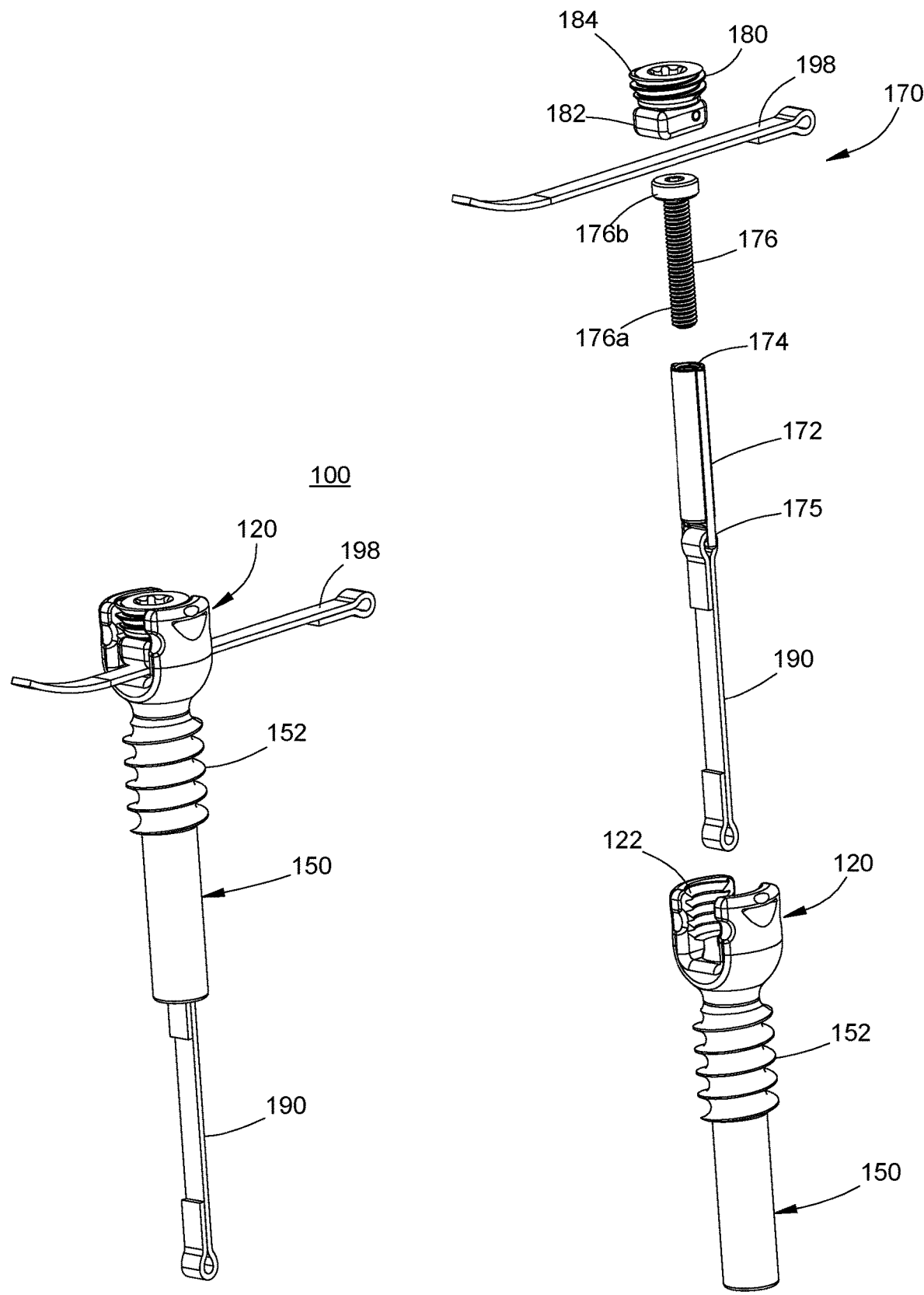
FIG. 20 is a perspective view of another of a band tensioner provided in accordance with the present disclosure.
FIG. 21 is an exploded view, with parts separated, of the band tensioner of FIG. 21.
Figure 22:
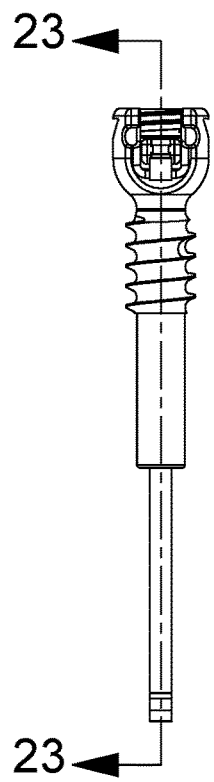
FIG. 22 is a side view of the band tensioner of FIG. 20 in a first position.
Figure 23:
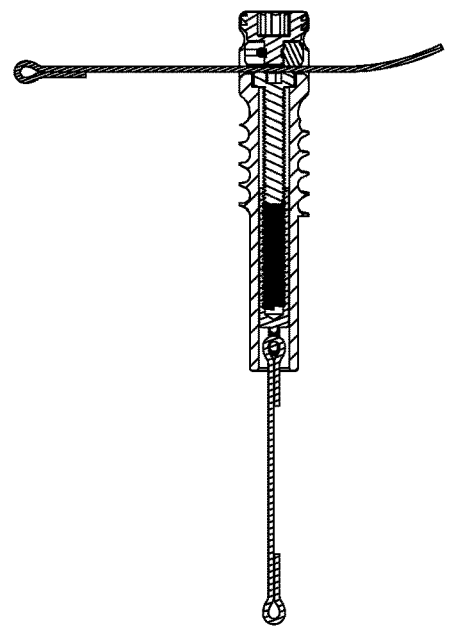
FIG. 23 is a cross-sectional view taken along the section line 23-23 of FIG. 22.
Figure 24:
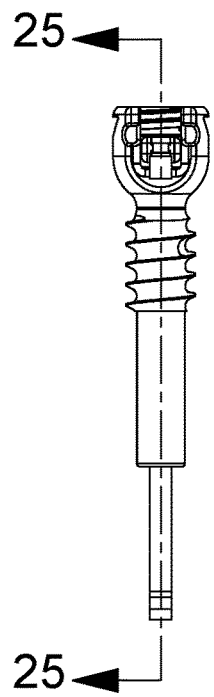
FIG. 24 is a side view of the band tensioner of FIG. 20 in a second position.

With particular reference to FIGS. 18 and 19, with the tip 960 of the alignment tool 950 engaged with the front portion 28b of the tensioning opening 28, the driver 900 is passed through a driver channel 980 of the alignment tool 950 until the tip 910 of the driver 900 engages the drive gear 72 of the tensioning mechanism 70. The driver 900 may be rotated to rotate the drive gear 72 such that the band shaft 80 is rotated in the first and second directions to tension and relax the flexible band 90 relative to the band tensioner 10. The handle 970 of the alignment tool 950 may be used to stabilize the band tensioner 10 during rotation of the driver 900. It is contemplated that the driver 900 may be used to manipulate the drive gear 72 without the use of the alignment tool 950.

The driver 900 may be used to tension or relax the flexible implant 90. Initially, the driver 900 is aligned with the drive axis D-D of the drive gear 72. The tip 910 of the driver 900 is inserted through the tensioning opening 28a of the head 20 to engage the drive socket 73 of the drive gear 72. The tip 910 of the driver 900 may have a shape complementary to a shape of the drive socket 73 such that the driver 900 rotatably fixed to the drive gear 72. With the tip 910 fixed to the drive gear 72, the driver 900 can be rotated in the first drive direction to extend the loop 92 away from the band tensioner 10 and can be rotated in the second drive direction to retract the loop 92 towards the band tensioner 10.

Referring back to FIGS. 1 and 2, the spinal construct 1 and assembly of the spinal construct 1 is described is accordance with the present disclosure. Initially, the band tensioner 10 is secured to a bony element, e.g., a vertebra of a spine. When the band tensioner 10 is secured to respective bony elements, the shank 50 of the band tensioner 10 may pass entirely through the bony element such that the band channel 54 (FIG. 9) of the band tensioner 10 exits an opposite side of the bony element from a head 20 of the band tensioner 10.

With the band tensioner 10 secured to the bony element, a flexible implant 90 is secured to the band tensioner 10. Referring briefly to FIG. 9, the central portion 96 may be positioned within the band tensioner 10 by passing the loop 92 through the band opening 26 in the top surface 25 of the head 20, through the band slot 87 in the slotted section 86 of the band shaft 80, and through the band channel 54 such that the loop 92 passes through the band tensioner 10. With the loop 92 passed through the band tensioner 10, a portion of the spinal construct (not shown) is positioned within the loop 92. Alternatively, the portion of the spinal construct may be positioned within the loop 92 and the free ends 94 of the flexible implant 90 may be passed through the band channel 54, through the band slot 87 in the slotted section of the band shaft 80, and through the band opening 26.

With brief reference to FIG. 10, the flexible implant 90 may also be secured to the band tensioner 10 through the side opening 24 of the head 20, the band slot 87, and the band opening 26 by a forward method, i.e., passing the loop 92 through the band opening 26, or a reverse method, i.e., passing the free ends 94 through the side opening 24.

With the flexible implant 90 secured to the band tensioner 10 and the portion of the spinal construct, the driver 900 is used to tension the flexible implant 90. Specifically, the tip 910 of the drive 900 (FIG. 19) is engaged with the drive gear 72 of the band tensioner 10 to tension the flexible implant 90.

Figure 25:
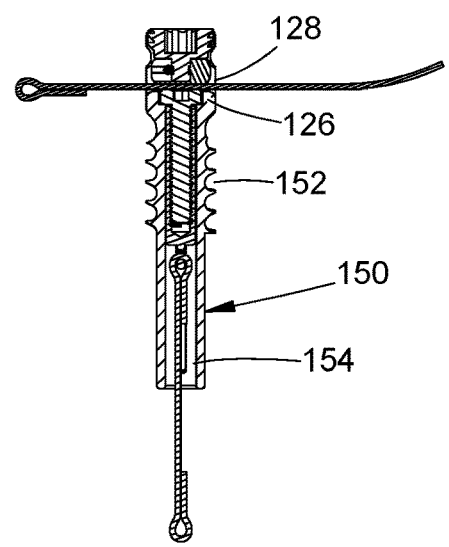
FIG. 25 is a cross-sectional view taken along the section line 25-25 of FIG. 24.
Figure 27:
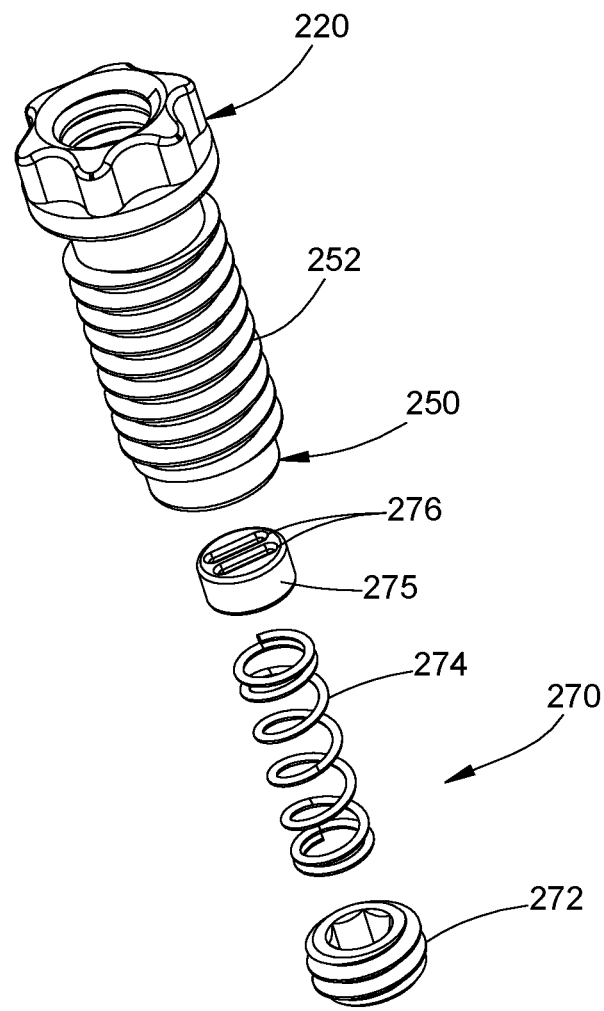
FIG. 27 is an exploded view, with parts separated, of the band tensioner of FIG. 26.
Figure 26:
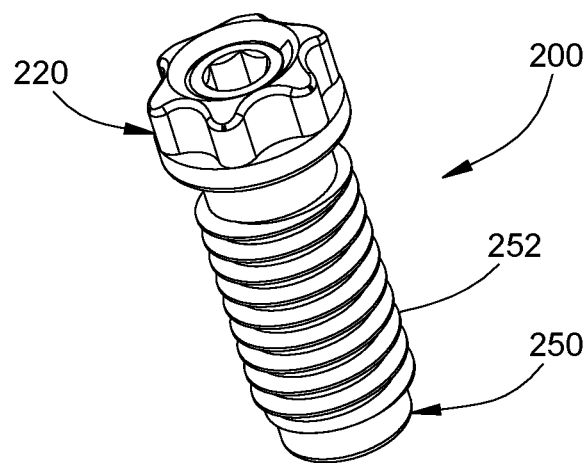
FIG. 26 is a perspective view of another band tensioner provided in accordance with the present disclosure.
Figure 28:
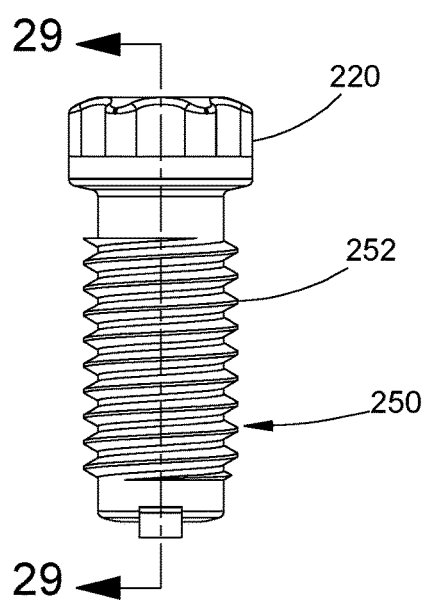
FIG. 28 is a side view of the band tensioner of FIG. 26.

Referring to FIGS. 20-25, another band tensioner 100 is disclosed in accordance the present disclosure. The band tensioner 100 includes a head 120, a shank 150, and a tensioning mechanism 170. The shank 150 is similar to the shank 50 detailed above with respect to the band tensioner 10 with similar elements represented with similar labels with a "1" preceding the previous label. The tensioning mechanism 170 includes a sleeve 172 that is slidably received within a band channel 154 of the shank 150. The sleeve 172 defines a threaded hole 174 and a band slot 175. The band slot 175 is configured to receive a portion of a flexible band 190 that passes through the band channel 154 of the shank 150. The threaded hole 174 receives a tensioning screw 176 that is threaded into the threaded hole 174. The tensioning screw 176 includes a threaded shank 176*a* that is received into the threaded hole 174 and a stop 176*b* that is received by the head 120 to longitudinally fix the tensioning screw 176 relative to the head 120. The head 120 may include a stop recess 126 that receives the stop 176*b* (FIG. 25). The tensioning screw 176 can be rotated in a first direction to draw the sleeve 172 proximally such that the flexible band 190 is tensioned and can be rotated in a second direction such that the sleeve 172 is moved distally such that the flexible band 190 is relaxed. The stop 176*b* may include an engagement opening, e.g., a hexagonal opening, a slot, two crossing slots, that allow for the rotation of the tensioning screw 176 relative to the shank 150. The tensioning mechanism also includes a lock screw 180 having thread 184 threadably engage threads 122 defined in the head 120. The lock screw 180 includes a chock 182 distal of the threads 184 that is configured to engage a flexible band 198 that passes between the stop 176*b* and the lock screw 180 to lock the flexible band 198 relative to the head 120. It will be appreciated that the flexible band 198 passes through the head 120 in a direction transverse to a longitudinal axis of the shank 150. The head 120 may define a band slot 128 to receive the flexible band 198. While the flexible band 190 and the flexible band 198 are shown as two separate bands, it is contemplated that the flexible band 190 and the flexible band 198 are two end portions of a single flexible band that passes around a bony element and/or a portion of a spinal construct.

Figure 29:
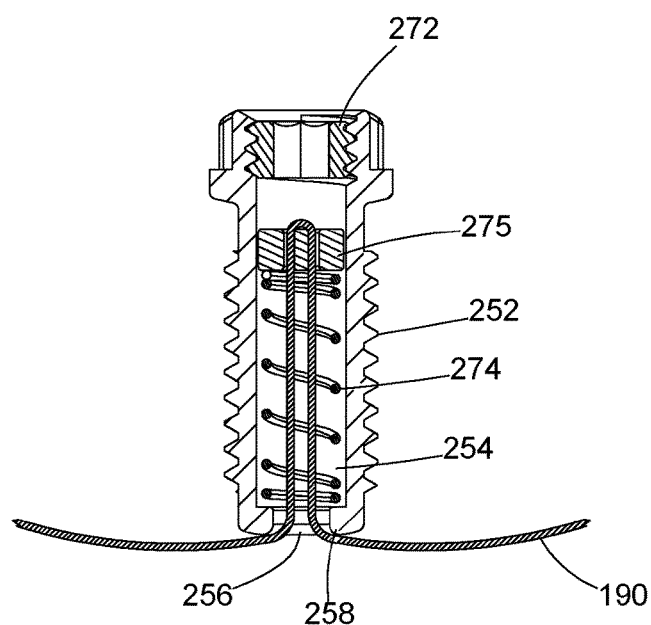
FIG. 29 is a cross-sectional view taken along the section line 29-29 of FIG. 28.

With reference to FIGS. 26-29, another band tensioner 200 is disclosed in accordance with the present disclosure. The band tensioner 200 includes a head 220 and a shank 250. The shank 250 includes a threaded portion 252 and defines a band channel 254 therethrough. With particular reference to FIG. 29, a distal portion of the shank 250 defines an opening 256 that has a reduced diameter relative to the band channel 254 such that ledges 258 are formed. The band tensioner 200 also includes a tensioning mechanism 270 that is received within the band channel 254. The tensioning mechanism 270 includes a biasing member 274 and a band retainer 275. The biasing member 274 is received within the band channel 254 and is configured to urge the band retainer 275 proximally, i.e., towards the head 220 of the band tensioner 200. The ledges 258 prevent the biasing member 274 from passing distally through the opening 256. The biasing member 274 may be a coil spring or another biasing member suitable for biasing the band retainer 275 proximally. The band retainer 275 defines band slots 276 that are configured to receive a flexible band 190 therethrough. As shown in FIG. 29, the flexible band 190 enters through the opening 256, through the biasing member 274, through one of the band slots 276, out the other band slot 276, back through the biasing member 274, and out of the opening 256 such that as the band retainer 275 is moved proximally by the biasing member 274 is tensioned and as a force applied to the flexible band 190 draws the band retainer 275 distally against the biasing member 274 the flexible band 190 is relaxed. The tensioning mechanism 270 may include a retention screw 272 that is received within the head 220 to prevent the remainder of the tensioning mechanism 270 from passing proximally through the head 220. It will be appreciated that the retention screw 272 allows for easy assembly of the tensioning mechanism 270 outside of the band channel 254 and then allows the tensioning mechanism 270 to be secured within the band channel 254.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A band tensioner comprising:
a shank configured to secure the band tensioner to a first bony element;
a head secured to an end of the shank; and
a tensioning mechanism disposed within the head and configured to lengthen and shorten a flexible implant relative to the head of the band tensioner, the tensioning mechanism including a band shaft and a drive gear, wherein the tensioning mechanism includes a retainer that is received within the head and engaged with the band shaft and the drive gear such that the retainer receives the drive gear to secure the band shaft and the drive gear within the head.

2. The band tensioner according to claim 1, wherein;
the band shaft defines a shaft axis and a slot therethrough, the slot is configured to receive a portion of the flexible implant such that the flexible implant is wound around the band shaft in response to rotation of the band shaft about the shaft axis in a first direction and is unwound from about the shaft in response to rotation of the band shaft about the shaft axis in a second direction opposite the first direction.

3. The band tensioner according to claim 2, wherein;
the drive gear defines a drive axis, the drive gear operably associated with the band shaft such that rotation of the drive gear in a first drive direction about the drive axis rotates the band shaft in the first direction and rotation of the drive gear in a second drive direction opposite the first drive direction rotates the band shaft in the second direction.

4. The band tensioner according to claim 3, wherein the drive axis is perpendicular to the shaft axis.

5. The band tensioner according to claim 2, wherein;
the shank defines a longitudinal axis of the band tensioner, the shaft axis perpendicular to the longitudinal axis.

6. The band tensioner according to claim 1, wherein;
the shank defines a channel that passes therethrough, the shank configured to pass entirely through a bony element such that the channel is defined entirely through the bony element.

7. A spinal construct comprising:
a flexible implant; and
a band tensioner including:
a shank configured to secure the band tensioner to a bony element;
a head secured to an end of the shank; and
a tensioning mechanism disposed within the head and configured to lengthen and shorten the flexible implant relative to the head of the band tensioner, the tensioning mechanism including a band shaft and a drive gear, wherein the tensioning mechanism includes a retainer that is received within the head and engaged with the band shaft and the drive gear such that the retainer receives the drive gear to secure the band shaft and the drive gear within the head.

8. The spinal construct according to claim 7, wherein;
the a band shaft defines a shaft axis and a slot therethrough, the slot receiving a portion of the flexible implant such that the flexible implant is wound around the band shaft in response to rotation of the band shaft about the shaft axis in a first direction and is unwound from about the shaft in response to rotation of the band shaft about the shaft axis in a second direction opposite the first direction.

9. The spinal construct according to claim 8, wherein;
the drive gear defines a drive axis, the drive gear operably associated with the band shaft such that rotation of the drive gear in a first drive direction about the drive axis rotates the band shaft in the first direction and rotation of the drive gear in a second drive direction opposite the first drive direction rotates the band shaft in the second direction.

10. The spinal construct according to claim 9, wherein;
the drive axis is perpendicular to the shaft axis.

11. The spinal construct according to claim 7, wherein;
the shank defines a channel that passes therethrough, the shank configured to pass entirely through a bony element such that the channel is defined entirely through the bony element.

12. A method of correcting a defect of a spine, the method comprising:
securing a shank of a band tensioner to a vertebra of the spine;
securing a flexible implant within a tensioning mechanism of the band tensioner; and
tensioning the flexible implant with the tensioning mechanism,
wherein the tensioning mechanism includes a band shaft, a drive gear and a retainer received within a head of the band tensioner, wherein the retainer receives the drive gear to secure the band shaft and the drive gear within the head, and tensioning the flexible implant with the tensioning mechanism includes engaging the retainer with the band shaft and the drive gear.

13. The method according to claim 12, wherein;
securing the band tensioner to the vertebra includes passing the shank of the band tensioner through the vertebra.

14. The method according to claim 13, wherein;
securing the flexible implant within the tensioning mechanism includes passing the flexible implant through a channel defined by the shank such that the flexible implant passes entirely through the vertebra.

15. The method according to claim 12, wherein;
securing the flexible implant within the tensioning mechanism includes passing the flexible implant through a slot defined in a band shaft of the tensioning mechanism.

16. The method according to claim 15, wherein;
tensioning the flexible implant includes rotating the band shaft about a shaft axis such that the flexible implant is wound around the band shaft.

17. The method according to claim 12, wherein;
securing the band tensioner to the vertebra includes passing a tip of a driver through a first opening in the head of the band tensioner to rotate the band tensioner about a longitudinal axis thereof to thread the shank of the band tensioner into the vertebra.

18. The method according to claim 17, wherein;
tensioning the flexible implant includes passing the tip of the driver through a second opening in the head of the band tensioner which is offset from the first opening to rotate the drive gear of the tensioning mechanism.

19. The method according to claim 12, wherein;
tensioning the flexible implant includes engaging an opening in the head with a tip of an alignment tool to rotatably fix the band tensioner about a longitudinal axis thereof and passing a driver through a driver channel of the alignment tool such that a tip of the driver passes through the tip of the alignment tool to engage the drive gear of the tensioning mechanism.

* * * * *